(12) United States Patent
Rongione et al.

(10) Patent No.: US 8,203,012 B2
(45) Date of Patent: Jun. 19, 2012

(54) PROCESS FOR PREPARING CONJUGATED LINOLEIC ACID AND DERIVATIVES THEREOF FROM RICINOLEIC ACID

(75) Inventors: Joseph C. Rongione, Middleton, NJ (US); Jenifer Heydinger Galante, Oakland, NJ (US); Randal J. Bernhardt, Antioch, IL (US)

(73) Assignee: Stepan Company, Northfield, IL (US)

( * ) Notice: Subject to any disclaimer, the term of this patent is extended or adjusted under 35 U.S.C. 154(b) by 568 days.

(21) Appl. No.: 11/991,688

(22) PCT Filed: Dec. 5, 2006

(86) PCT No.: PCT/US2006/046515
§ 371 (c)(1),
(2), (4) Date: Sep. 29, 2009

(87) PCT Pub. No.: WO2007/070302
PCT Pub. Date: Jun. 21, 2007

(65) Prior Publication Data
US 2010/0036142 A1    Feb. 11, 2010

(51) Int. Cl.
*C07B 37/00* (2006.01)
(52) U.S. Cl. ............... 554/127; 554/224
(58) Field of Classification Search .............. None
See application file for complete search history.

(56) References Cited

U.S. PATENT DOCUMENTS

| | | | |
|---|---|---|---|
| 3,162,658 A | 12/1964 | Baltes et al. | |
| 3,984,444 A | 10/1976 | Ritz et al. | |
| 4,185,027 A | 1/1980 | Logan | |
| 5,428,072 A | 6/1995 | Cook et al. | |
| 5,554,646 A | 9/1996 | Cook et al. | |
| 5,872,289 A | 2/1999 | Appleby et al. | |
| 6,015,833 A | 1/2000 | Saebo et al. | |
| 6,019,990 A | 2/2000 | Remmereit | |
| 6,034,132 A | 3/2000 | Remereit | |
| 6,042,869 A | 3/2000 | Remmereit | |
| 6,060,514 A | 5/2000 | Jerome et al. | |
| 6,153,774 A | 11/2000 | Seidel | |
| 6,160,140 A | 12/2000 | Bhaggan et al. | |
| 6,203,843 B1 | 3/2001 | Remmereit | |
| 6,225,486 B1 | 5/2001 | Saebo et al. | |
| 6,242,621 B1 | 6/2001 | Jerome et al. | |
| 6,319,950 B1 | 11/2001 | Seidel | |
| 6,333,353 B2 | 12/2001 | Saebo et al. | |
| 6,380,409 B1 | 4/2002 | Saebo et al. | |
| 6,420,577 B1 | 7/2002 | Reaney et al. | |
| 6,479,683 B1 | 11/2002 | Abney et al. | |
| 6,524,527 B2 | 2/2003 | Fimreite et al. | |
| 6,610,868 B2 | 8/2003 | Saebo et al. | |
| 6,677,470 B2 | 1/2004 | Saebo et al. | |
| 6,743,931 B2 | 6/2004 | Saebo et al. | |
| 6,897,327 B2 | 5/2005 | Rongione et al. | |
| 2004/0058998 A1 | 3/2004 | Saebo et al. | |
| 2004/0225141 A1 | 11/2004 | Rongione et al. | |
| 2004/0225142 A1 | 11/2004 | Saebo et al. | |

FOREIGN PATENT DOCUMENTS

| | | |
|---|---|---|
| GB | 1589314 | 5/1981 |
| WO | WO 9707187 | 2/1997 |
| WO | WO 0114304 | 3/2001 |
| WO | WO 0222768 | 3/2002 |
| WO | WO 2004015046 | 2/2004 |
| WO | WO 2004029186 | 4/2004 |

OTHER PUBLICATIONS

International Search Report corresponding to International Application No. PCT/US2006/046515, dated Oct. 2, 2007, 1 page.
International Search Report corresponding to International Application No. PCT/US2006/046515, dated Oct. 3, 2007, 2 pages.
Written Opinion of the International Searching Authority corresponding to International Application No. PCT/US2006/046515, dated Oct. 3, 2007, 6 pages.
International Search Report corresponding to International Application No. PCT/US2004/012387, mailed Mar. 18, 2005, 2 pages.
Written Opinion of the International Searching Authority corresponding to International Application PCT/US2004/012387, mailed Mar. 18, 2005, 5 pages.
Supplementary European Search Report corresponding to European Patent Application No. 04760826.0-2103, completed Aug. 24, 2006, 3 pages.
International Preliminary Report on Patentability corresponding to International Application No. PCT/US2004/012387, issued Nov. 11, 2005, 4 pages.
Communication from the European Patent Office corresponding to European Patent Application No. 04 760 826.0-1211, dated May 2, 2007, 7 pages.
European Search Report corresponding to European Patent Application Serial No. 06847505.2-1211, mailed Oct. 21, 2008, 5 pages.
Yang et al., "Production of conjugated linoleic acids through KOH-catalyzed dehydration of ricinoleic acid", Chemistry and Physics of Lipids, vol. 119, 2002, pp. 23-31.
Berdeaux et al., "Large-Scale Synthesis of Methyl cis-9, trans-11-Octadecadienoate from Methyl Ricinoleate", Journal of the American Oil Chemists' Society, Springer, Berlin, vol. 74, No. 8, Jan. 1, 1997, pp. 1011-1015.

*Primary Examiner* — Yate K Cutliff
(74) *Attorney, Agent, or Firm* — McAndrews, Held & Malloy, Ltd.

(57) ABSTRACT

A process for preparing conjugated linoleic acid (CLA) or derivatives thereof from ricinoleic acid, lower alkyl esters of ricinoleic acid, or salts thereof. The CLA is formed by reacting a carboxylic acid, or anhydride, anhydride equivalent, or ester thereof with the ricinoleic acid or derivative to form an intermediate having a carboxylic ester at the 12-hydroxy position of the ricinoleic acid or derivative, and reacting the intermediate with a base to form a cis-9, trans-11 conjugated linoleic acid.

22 Claims, No Drawings

PROCESS FOR PREPARING CONJUGATED LINOLEIC ACID AND DERIVATIVES THEREOF FROM RICINOLEIC ACID

FIELD OF THE INVENTION

The presently described technology relates to an improved process for manufacturing conjugated linoleic acids (CLAs) and derivatives thereof from acylated ricinoleic acid, lower alkyl esters of acylated ricinoleic acid, or salts thereof. The process involves acylating the hydroxyl group at the 12 position of the ricinoleic acid, or ester or salt thereof, utilizing a carboxylic acid, or anhydride or ester thereof, to accomplish the acylation, and then using a base to eliminate the carboxylic ester from acylated ricinoleic acid or derivative to form the conjugated linoleic acid or derivative.

BACKGROUND OF THE INVENTION

Conjugated linoleic acids (CLAs) refers to a mixture of positional and geometric isomers of linoleic acids, which are unsaturated fatty acids considered essential to the human diet and found preferentially in dairy products and meat. CLAs have generated much interest in the academic and business communities because of their nutritional, therapeutic, and pharmacological properties. There are numerous known CLA compositions, along with various known routes to prepare such compositions. See, e.g., U.S. Pat. Nos. 6,420,577 (Reaney et al.); U.S. Pat. No. 6,015,833 (Saebo et al.); U.S. Pat. No. 6,160,140 (Bhaggan et al.); U.S. Pat. No. 6,034,132 and U.S. Pat. No. 6,019,990 (both to Remmerelt); and U.S. Pat. No. 6,225,486 (Saebo et al.). CLAs have become biologically and commercially important, as they have been observed to inhibit mutagenesis and to provide unique nutritional value.

Typically, CLAs are a mixture of positional isomers of linolelc acid (C18:2) having conjugated double bonds. The cis-9, trans-11 and trans-10, cis-12 isomers are present in greatest abundance in typical CLA compositions, but it is not absolutely certain which isomers are responsible for the biological and heightened nutritional activity observed. It has been noted from labeled uptake studies that the 9,11 isomer appears to be somewhat preferentially taken up and incorporated into the phospholipid fraction of animal tissues, and to a lesser extent the 10,12 isomer. (See Ha et al., Cancer Res., 50:1097 (1991)).

The properties of unsaturated fatty acids and their derivatives can be altered by rearrangement, i.e., isomerization, of the structure of the double bond, either with respect to the steric position or the position in the carbon chain of the molecule of the fatty acid. As noted above, conjugated fatty acid derivatives are of great technical and commercial interest and, therefore, many attempts have been made to isomerize unconjugated fatty acids to conjugated ones. Without being bound by any particular theory, it is believed that such a shifting of the double bond is possible because the conjugated form has a lower state of energy than the unconjugated form.

Previously known routes to produce conjugated unsaturated compounds include hydrogenation of fats using a variety of catalysts. These routes, however, often lead to incomplete isomerization and unwanted side reactions, such as polymerization and intramolecular cyclization. Other known routes include isomerization with an excess of alkali metal hydroxide in an aqueous or alcoholic medium, which leads to a quantitative isomerization. However, this route suffers from the limitation that a considerable excess of alkali metal hydroxide must be used, so that the conjugated fatty acids or fatty acid compounds are obtained in the form of their alkali soaps and have to be recovered and isolated accordingly. These techniques differ in the use of a particular solvent, temperature and pressure. See, e.g., U.S. Pat. No. 3,162,658 (Baltes et al.).

The rearrangement of the double bonds of linoleic acids to conjugated positions has been shown to occur during treatment with catalysts such as nickel or alkali at high temperatures, and during auto oxidation. Theoretically, eight possible geometric isomers of 9,11 and 10,12 octadecadienoic acid (c9, c11; c9, t11; t9, c11; t9, t11; c10, c12; c10, t12; t10, c12 and t10, t12) would result from the isomerization of c9, c12-octadecadienoic acid. Again, without being bound by any particular theory, a general mechanism for the isomerization of linoleic acids has been described by J. C. Cowan in JOACS 72:492-99 (1950). The formation of certain isomers of CLAs is thermodynamically favored as described therein. The relatively higher distribution of 9,11 and 10,12 isomers apparently results from the further stabilization of the c9, t11 or t10, c12 geometric isomers.

U.S. Pat. No. 6,420,577 (Reaney et al.) describes a process for making CLAs by reacting a linoleic acid-rich oil with a base, in the presence of a catalytic amount of such a base, in an aqueous medium via simultaneous saponification and quantitative isomerization. However, this process utilizes a heightened temperature (>170° C.). Higher temperatures lead to the formation of undesirable CLA isomers, including the trans, trans-CLA isomers.

U.S. Pat. No. 6,160,140 (the '140 patent), claims the conversation of a linoleic acid-containing oil, free fatty acid or alkyl ester to CLAs by treating it with a base in an alcohol solution, where the alcohol has at least 3 carbons and at least 2 hydroxyl groups. The preferred embodiment of the '140 patent is to use potassium hydroxide in propylene glycol. The use of solvent in the conjugation (isomerization) step gives rise to the potential formation of unwanted CLA-alcohol esters (e.g., CLA-propylene glycol esters).

U.S. Pat. No. 3,162,658 (the '658 patent), describes the use of alkali metal hydrocarbyl alcoholates or alkali metal amides to isomerize esters of unconjugated polyethylene acids such as linoleic acids. But it uses polar solvents for the isomerization step, which is undesirable. The '658 patent also makes no mention of converting the resultant conjugated esters to the corresponding acids.

U.S. Pat. No. 3,984,444 (Ritz et al., the '444 patent), describes the isomerization of an ester of an alcohol having 1 to 12 carbon atoms and a fatty acid having 10 to 24 carbon atoms and isolated double bonds to the corresponding compound having conjugated double bonds using alkaline metal alcoholates in strongly polar aprotic solvents. As noted above, the use of solvents in the conjugation step is undesirable. The '444 patent does not teach how to convert the resultant conjugated esters to the corresponding acids as well.

Typical procedures for the conversation of fatty acid methyl esters (FAME) to fatty acids (FA), such as those described in U.S. Pat. Nos. 4,185,027 and 5,872,289, involve the use of acidic catalysts. The use of such acidic catalysts is undesirable.

WO 01/14304 uses steam in the presence of a catalyst to directly hydrolyze FAME to FA. The reaction is carried out at a heightened temperature, which leads to the formation of undesirable CLA isomers, including the trans, trans-CLA isomers. Similarly, WO 97/07187 uses near critical temperatures and supercritical pressures to accomplish the transformation of FAME to FA.

GB 1589314 uses alkali metal hydroxides in alkyl nitrile solution for the conversation of FAME to FA.

U.S. Pat. Nos. 5,892,074 and 6,153,774 describe a process for making CLA enriched in the c9, t11 isomer from methyl ricinoleate by forming mesylate or tosylate esters at the 12 hydroxy position and reacting the diester with a strong organic base, 1,8-diazabicyclo[5.4.0]undec-7-ene (DBU). The sulfonyl halides used as the derivatizing agent, however, liberate corrosive hydrogen halides that must be scrubbed from the process effluent gas and neutralized. In addition, the organic byproduct resulting from treatment with the organic base is an organic amine salt of a sulfonic acid which must be completely removed if the CLA is to be used as a food supplement. Further, the organic base used is a fairly expensive organic amine.

PCT Application No. WO 118161 A2 discloses a process similar to that disclosed in U.S. Pat. Nos. 5,892,074 and 6,153,774, but uses castor oil instead of methyl ricinoleate as a starting component. The process suffers from the same drawbacks outlined above using methyl ricinoleate as a starting component. In addition, the process treats the tosylate or mesylate compounds with a mineral acid, which further complicates the recovery of material from the process.

*Chemistry and Physics of Lipids*, 2002, 119, 23-31 describes the use of potassium hydroxide to cause the elimination of the mesylate ester of methyl ricinoleate. This process also suffers from the same drawbacks that come with the use of a sulfonyl halide.

There exists a need for an improved process to produce CLA which is enriched with the highly desired c9, t11 isomer. Additionally, there is a need for an improved process to readily and economically produce such CLA compositions in a safer and more environmentally friendly way.

BRIEF SUMMARY OF THE INVENTION

CLAs made by conventional treatment of a linoleic oil (e.g., safflower, sunflower) or an alkyl linoleate composition with a basic catalyst, such as potassium hydroxide, contain relatively high levels of undesirable isomers (e.g., trans-11, trans-13, trans-8, trans-10; trans-9, cis-11; and cis-10 trans-12 CLA). The process of the present technology, however, produces conjugated linoleic acid-containing fatty acids which are enriched in desirable cis-9, trans-11 CLA isomers, but contain very small amounts of undesirable isomers. It is an object of the present technology to provide a process to produce compositions containing high levels of desirable CLA isomers.

Various aspects of the present technology are directed to processes for producing conjugated linoleic acids (CLAs) or derivatives thereof which are enriched in desirable CLA isomers, utilizing ricinoleic acid or a derivative thereof as a starting component. More specifically, at least one aspect of the present technology is directed to a process for producing a conjugated linoleic acid or a derivative thereof comprising the steps of reacting a ricinoleic acid or derivative thereof with a carboxylic acid, ester, anhydride, or anhydride equivalent thereof to form an acylated intermediate comprising a carboxylic ester of the ricinoleic acid or derivative thereof; and reacting the intermediate with a base to remove the carboxylic ester from the ricinoleic acid or derivative thereof to form a conjugated linoleic acid or derivative thereof. Such a process can involve reacting the ricinoleic acid or derivative thereof with a carboxylic acid, or a carboxylic ester, anhydride, or anhydride equivalent, to form an intermediate comprising an acylated ricinoleic acid or derivative thereof having a carboxylic ester at the 12 position, and then reacting the intermediate with a base to remove the carboxylic ester from the acylated ricinoleic acid or derivative and form the CLA.

The present process uses a carboxylic acid or derivatives thereof, including anhydrides, anhydride equivalents, or esters, as the derivatizing agent, which is less expensive and more environmentally friendly than the mesylate or tosylate derivatizing agents utilized by the prior art. In particular, use of a carboxylic acid or derivative thereof decreases processing time, decreases the size and toxicity of process waste streams, and avoids the use of sulfonyl halides which liberate corrosive hydrogen halides that can cause problems in an industrial environment. In addition, the process of the present technology can use an inexpensive alkoxide as the base for cleaving the carboxylate leaving group from the 12 position, rather than an expensive organic amine. Advantageously, the by-product of the process of the present technology is a salt of a carboxylic acid, which can easily be removed and will not interfere with the food grade status of the resulting CLA, whereas the by-product of the prior art is an organic amine salt of a sulfonic acid, which must be substantially completely removed by purification processes.

The intermediate formed as a result of the reaction of ricinoleic acid or a derivative thereof with the carboxylic acid, or ester, anhydride, or anhydride equivalent thereof, is an acylated ricinoleic acid or ricinoleate, which is more readily purified by distillation than either methyl ricinoleate, sulfonic esters of ricinoleate formed as a result of prior art processes, or the methyl ester of conjugated linoleic acid. This allows for the preparation of extremely high purity derivatives of the resulting c9, t11 conjugated linoleic acid.

DETAILED DESCRIPTION OF THE INVENTION

Definitions and Conventions

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11,13 octadecadienoic acid. As used herein, "CLA" encompasses a single isomer, a selected mixture of two or more isomers, and a non-selected mixture of isomers obtained from natural sources, as well as synthetic and semi-synthetic CIA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g, methanol, ethanol, propanol). Therefore, an ester of CLA or esterified CLA may contain any of the positional and geometric isomers of CLA.

It is intended that "undesirable isomers" of CLA include, but are not limited to c11, t13; t11, c13; t11, t13; c11, c13; c8, t10; t8, t10; c8, c10; and trans-trans isomers of octadecadienoic acid.

As used herein, "c" encompasses a chemical bond in the cis orientation, and "t" refers to a chemical bond in the trans orientation. If a positional isomer of CLA is designated with a "c" or a "t," then that designation includes all four possible isomers. For example, 10,12 octadecadienoic acid encompasses c10, t12; t10, c12; t10, t12; and c10, c12 octadecadienoic acid, while t10, c12 octadecadienoic acid or CLA refers to just the single isomer.

DESCRIPTION OF THE INVENTION

The process of the present technology encompasses a process for producing a conjugated linoleic acid, or derivative thereof, which is enriched in the c9, t11 isomer. The process comprises reacting a ricinoleic acid or derivative thereof, with a carboxylic acid, anhydride, anhydride equivalent, or ester thereof, wherein the ricinoleic acid or derivative is acylated at the 12 hydroxy position to form an acylated ricinoleic intermediate. The intermediate is then reacted with a base to eliminate the acyl group, i.e., the carboxylic ester, from the 12 position to form the conjugated linoleic acid.

The ricinoleic acid or derivatives thereof used as a starting component can be obtained from castor oil. Suitable derivatives of ricinoleic acid for use herein include, but are not limited to, alkyl esters of ricinoleic acid and non-toxic salts of ricinoleic acid. The alkyl esters can be obtained by esterification using short chain $C_1$-$C_6$ alcohols or any other suitable alcohol. A preferred alkyl ester of ricinoleic acid for use herein is methyl ricinoleate. The non-toxic ricinoleic acid salts that can be used in the present process include, but are not limited to, sodium, potassium and calcium ricinoleic acid salts.

The ricinoleic acid or derivative is reacted with a carboxylic acid, or an anhydride or ester thereof, to form an intermediate comprising an acylated ricinoleic acid or derivative. The intermediate can be formed using three alternative synthetic routes or pathways, each of which will achieve the same intermediate. The synthetic routes are (1) directly acylating the ricinoleic acid or derivative at the 12 hydroxy position by reaction with a carboxylic acid anhydride or carboxylic anhydride equivalent, (2) esterification at the 12 hydroxy position by a carboxylic acid, or (3) by transesterification at the 12 hydroxy position with an ester of a carboxylic acid.

In the direct acylation route to forming the acylated ricinoleic acid or derivative intermediate, the carboxylic acid anhydride is mixed with the ricinoleic acid or derivative, in the ratio of about 1 to about 5 equivalents of acylating agent to ricinoleic acid equivalent. Suitable carboxylic acid anhydrides for use in this direct acylation route include, but are not limited to linear or branched carboxylic anhydrides having from 2 to 10 carbons. One particular useful carboxylic acid anhydride is trimethyl acetic anhydride.

The direct acylation route can also be performed with a carboxylic anhydride equivalent Equivalents of carboxylic anhydride are those carboxylic derivatives that have a leaving group attached to the carbonyl moiety that facilitates the acylation reaction. Such leaving groups are halides (acyl halides), carbonates, other carboxylate species (e.g., mixed anhydrides) or heteroatom derivatives, such as for example, imidazolides (imidazole leaving group).

The acylation reaction is typically performed at temperatures ranging from about 60° C. to about 120° C. to increase the rate of reaction. Although not absolutely required, a catalyst may also be used to promote the acylation reaction. Suitable catalysts for use herein include mineral acids such as phosphoric or sulfuric acids, or sulfonic acids such as p-toluenesulfonic acid. The catalyst may be used in the amount of about 0.1 to about 2% based on the weight of the starting ricinoleic acid or derivative.

Similarly, the use of a solvent for the acylation reaction is not absolutely required. However, if a solvent is used, it may be, for example a nonpolar hydrocarbon such as hexane or heptane, a solvent of intermediate polarity such as acetone, acetonitrile or 2-butanone or a polar solvent such as dimethyl formamide (DMF) or dimethyl sulfoxide (DMSO). A useful amount of solvent is from about 0.5 to about 5:1 weight ratio based upon the weight of the starting ricinoleic acid or derivative and the carboxylic anhydride.

The acylation reaction results in the desired acylated ricinoleic intermediate and carboxylic acid byproducts. Such byproducts can be removed via a number of chemical or physical means known to those skilled in the art, such as distillation or basic aqueous washes.

In the alternative esterification pathway to obtain the acylated ricinoleic acid or derivative intermediate, a carboxylic acid is added to the ricinoleic acid or derivative in a ratio of about 1.1 to about 5 equivalents of carboxylic acid to ricinoleic acid equivalents. Suitable carboxylic acids include, but are not limited to, linear or branched carboxylic acids having from 2 to 10 carbons. The addition of a catalyst to promote the esterification reaction is not absolutely necessary. However, if a catalyst is added, it may be, for example, mineral acid such as phosphoric or sulfuric acids or sulfonic acids such as p-toluenesulfonic acid. The catalyst may be used in the amount of about 0.1 to about 3% based on the weight of the starting ricinoleic acid or derivative.

Similarly the use of a solvent for the esterification reaction is not absolutely necessary. However, if a solvent is used, it may be, for example, a nonpolar hydrocarbon such as hexane or heptane, a solvent of intermediate polarity such as acetone, acetonitrile or 2-butanone, or a polar solvent such as dimethyl formamide (DMF) or dimethyl sulfoxide (DMSO). The amount of solvent used may be from about 0.5 to about 5:1 weight ratio based on the weight of the starting ricinoleic acid and carboxylic acid.

The esterification reaction can be run at or slightly above the boiling point of the free carboxylic acid. If the reaction is run at a temperature above the boiling point of the carboxylic acid, it is convenient to include a partial condenser in the processing equipment. This partial condenser is set to a temperature that will condense the carboxylic acid back into the reaction mix while allowing the flow of water vapor from the reaction mix to an overhead receiver. Such a set up of processing equipment is well known to those skilled in the art. The water resulting from the reaction can be removed under vacuum or by means of a dehydrating agent, such as molecular sieves. The esterification route results in the same acylated ricinoleic acid or derivative intermediate as the direct acylation route utilizing the carboxylic acid anhydride.

In the alternative transesterification pathway to obtain the acylated ricinoleic acid or derivative intermediate, an ester of a carboxylic acid is reacted with the ricinoleic acid or derivative in a ratio of about 1.1 to about 5 equivalents of ester to ricinoleic acid equivalent. Suitable carboxylic acid esters include, but are not limited to, lower alkyl esters having 1 to 4 carbons, branched or linear, of lower alkyl carboxylic acids having 2 to 10 carbons, branched or linear. The carboxylic acid ester can be utilized as both a reagent and a solvent for the transesterification reaction.

The transesterification reaction is typically catalyzed by a base, but can also be performed under acidic or neutral conditions. Suitable basic catalysts are alkali metal or alkaline earth metal alkoxides and hydroxides. Preferred cations for the alkoxides or hydroxides are sodium, potassium and calcium, but lithium, cesium, magnesium copper, zinc, iron, tetraalkylammonium or tetraalkylphosphonium cations can also be used. If a catalyst is used, it is added in an amount of about 0.1 to about 4% based on the weight of the starting ricinoleic acid or derivative.

The transesterification reaction can be run at or below the boiling point of the lower boiling ester. Convenient processing equipment for conducting the reaction includes a reactor and a partial condenser set to allow the passage of the alcohol byproduct liberated during the reaction, while refluxing the starting carboxylic ester back to the reactor. The alcohol byproduct can be removed via distillation, either at atmospheric or reduced pressures. The reaction can be monitored through intermittent GC analyses which show the disappearance of the ricinoleic acid and the appearance of the acylated ricinoleic acid intermediate.

Regardless of which process route is selected to obtain the acylated ricinoleic acid intermediate, the intermediate will essentially have the same purity and, when reacted with a base, as further described herein, will result in the desired conjugated linoleic acid or derivative.

Once the acylated ricinoleic acid intermediate is formed, it is mixed with a base, and the system is heated to a temperature in the range of about 80° C. to about 160° C., more preferably about 80° C. to about 140° C., and most preferably to about 90° C. Alternatively, the intermediate can first be heated to a temperature in the range of about 80° C. to about 160° C. and the base can be added over a period of about 1 to about 4 hours. The base acts to remove the carboxylic ester from the 12 position of the ricinoleic acid intermediate, resulting in the formation of the desired c9, t11 conjugated linoleic acid or derivative thereof.

Suitable bases for cleaving the carboxylic ester include, but are not limited to, inorganics, alkali, alkaline earth or alkyl ammonium hydroxides, oxides, alkoxides, and carbonates, as well as organic bases, such as 1,8-diazabicyclo[5.4.0]undec-7-ene (DBU) and 1,5,7-triazabicyclo [4.4.0]dec-5-ene (TBD). Preferred cations for the base are sodium, potassium, or calcium, or a symmetrical lower tetraalkyl (14 carbons), dibenzyl dialkyl (1-4 carbons), benzyl trialkyl (1-4 carbons), or long chain alkyl (12-18 carbons), trialkyl (1-4 carbons) ammonium group. Preferred inorganic hydroxide cations can include sodium, potassium, or calcium. Suitable alkoxides include alkali or alkali earth alkoxide salts of a lower alkyl group alcohol (1-4 carbons, branched or linear). The base can be added to the reaction system as a solid or, alternatively, as a solution in the conjugate alcohol of the alkoxide. Alkoxide bases are advantageous for use herein because they are relatively inexpensive and because the byproducts resulting from the reaction of the intermediate with an alkoxide base are innocuous carboxylic acid salts.

The progress of the reaction of the base with the ricinoleic intermediate can be monitored by intermittent GC analyses. As the reaction progresses, the CLA content continues to increase at the expense of the acylated ricinoleic intermediate. Upon completion of the reaction, the byproducts, which comprise carboxylic acid salts, can be removed by washing or filtration and the conjugated linoleic acid or derivative can be recovered. The resulting CLAs are highly enriched in the desirable c9, t11 isomer.

The CLAs produced in accordance with the methods described herein have a variety of uses. These uses include, for example, the reduction of body fat in animals; increasing muscle mass in animals; reducing body weight in humans; attenuating allergic reactions in animals; preventing weight loss due to immune stimulation in animals; elevating CD-4 and CD-8 cell counts in animals; increasing the mineral content of bone in animals; preventing skeletal abnormalities in animals: and decreasing the amount of cholesterol in the blood of animals. In each case, the term "animal" includes all mammals, including humans.

The CLAs produced by the present technology may be incorporated into animal feeds, nutritional supplements, dietary applications, or pharmaceutical applications. The isomer enriched CLA may be formulated with suitable carriers such as starch, sucrose or lactose in tablets, pills, dragees, capsules, solutions, liquids, slurries, suspensions and emulsions. The isomer enriched CLA may be provided in aqueous solution or oily solution. The tablet, pill or capsule comprising the CLA may be coated with an enteric coating which dissolves at a pH of about 6.0 to 7.0. A suitable enteric coating which dissolves in the small intestine, but not in the stomach is cellulose acetate phthalate. In a preferred formulation, the isomer enriched CLA is provided as soft gelatin capsules. The isomer enriched CLA may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation and administration may be found in the latest edition of Remington's *Pharmaceutical Sciences* (Maack Publishing Co., Easton, Pa.).

The isomer enriched CLA produced by the present technology may also be provided as a supplement in various prepared food products and drinks. For the purposes of this application, prepared food product means any natural, processed, diet or non-diet food product to which isomer enriched CLA prepared by the present technology has been added. The isomer enriched CLA may be directly incorporated into various prepared food products, including, but not limited to diet drinks, diet bars, supplements, prepared frozen meals, candy, snack products (e.g., chips), prepared meat products, milk, cheese, yogurt and any other fat or oil containing foods.

In order to better understand the preferred embodiments and advantages of the present technology, reference may be had to the following examples. However, the examples should not be construed to limit the scope of the invention.

EXAMPLE 1

Conjugated Linoleic Methyl Esters (CLME) from Methyl Ricinoleate

Methyl ricinoleate (42.8 g, 0.137 mol) was dissolved in methyl trimethylacetate (methyl pivalate, 95.6 g, 0.823 mol). The solution was heated to 80° C. Potassium methoxide (40.3 g of a 25% methanol solution, 0.144 mol) was then added over 2 hours. Solids began to appear as the reaction was held at 80° C. GC analysis of the reaction mix at the end of the base addition showed 46.1% methyl 12-trimethylacetoxyoctadec-9 (Z)-enoate and 48.9% methyl ricinoleate. Continued monitoring of the reaction mix by GC showed the appearance of CLME at the expense of methyl ricinoleate. Five hours after the end of the base addition GC analysis showed 21.1% CLME (78% of which was the c9, t11 isomer), 52.1% methyl 12-trimethylacetoxyoctadec-9 (Z)-enoate and 21.8% methyl ricinoleate.

EXAMPLE 2

Formation of Methyl 12-trimethylacetoxyoctadec-9 (Z)-enoate

Methyl ricinoleate (65.6 g, 0.210 mol) was combined with trimethyl acetic anhydride (50.3 g, 0.270 mol). The solution was heated to 95° C. for 12 hours. The organic phase was washed with aqueous sodium bicarbonate and then dried under vacuum. GC analysis showed that 98.7% of the methyl ricinoleate had been esterified at the 12 position.

EXAMPLE 3

CLME from Methyl 12-trimethylacetoxyoctadec-9 (Z)-enoate

A portion of the methyl 12-trimethylacetoxyoctadec-9 (Z)-enoate from Example 2 (43.6 g, 0.110 mol) was heated to 100° C. Potassium methoxide solution (33.45 g, 25% solution in methanol, 0.119 mol) was added over 2.5 hours. After holding the reaction mix at 90° C. for 1 hour, GC analysis showed (excluding salts) CLME (48.4%/; 80.5% of which was the c9, t11 isomer), methyl linoleate (20.7%), starting methyl 12-trimethylacetoxyoctadec-9 (Z)-enoate (14.2%) and methyl ricinoleate (10.1%).

The present technology is now described in such full, clear, concise and exact terms as to enable any person skilled in the art to which it pertains, to practice the same. It is to be understood that the foregoing describes preferred embodiments of the invention and that modifications may be made therein without departing from the spirit and scope of the present invention as set forth in the appended claims.

The invention claimed is:

1. A process for producing a conjugated linoleic acid or an ester thereof comprising the steps of:
   (a) reacting a ricinoleic acid or ester or salt thereof with a carboxylic acid, a carboxylic ester, or a carboxylic anhydride, or a carboxylic derivative that has a leaving group attached to the carbonyl moiety and facilitates an acylation reaction to form an acylated intermediate comprising a carboxylic ester at the 12-hydroxy position of the ricinoleic acid or ester or salt thereof;
   (b) reacting the intermediate with a base to remove the carboxylic ester at the 12-hydroxy position from the ricinoleic acid or ester or salt thereof to form a conjugated linoleic acid or an ester thereof.

2. The process of claim 1, wherein the base is an alkali or alkaline earth alkoxide salt of a $C_1$-$C_4$ alkyl group alcohol.

3. The process of claim 1, wherein the base is an amine.

4. The process of claim 2, wherein the cation of the alkoxide salt is sodium, potassium or calcium.

5. The process of claim 2, wherein the base is a solid.

6. The process of claim 2, wherein the base is in solution in the alcohol of the alkoxide salt.

7. The process of claim 1, wherein the base is added to the intermediate at a temperature in the range of about 80° C. to about 160° C.

8. The process of claim 7, wherein the temperature is in the range of about 80° C. to about 140° C.

9. The process of claim 8, wherein the temperature is about 90° C.

10. The process of claim 3, wherein the amine is 1,8,-diazabicyclo [5.4.0] undec-7-ene or 1,5,7,-triazabicyclo [4.4.0] dec-5-ene.

11. The process of claim 1, wherein the base is an inorganic or an alkyl ammonium hydroxide.

12. The process of claim 11, wherein the inorganic hydroxide cation is sodium, potassium or calcium.

13. The process of claim 11, wherein the alkyl ammonium cation is selected from the group consisting of symmetrical tetra $C_1$-$C_4$ alkyl, benzyl tri $C_1$-$C_4$ alkyl, dibenzyl di $C_1$-$C_4$ alkyl, and $C_{12}$-$C_{18}$ alkyl, tri $C_1$-$C_4$ alkyl ammonium groups.

14. The process of claim 1, wherein the intermediate is formed by reacting a $C_2$-$C_{10}$ carboxylic anhydride or a $C_2$-$C_{10}$ carboxylic derivative that has a leaving group attached to the carbonyl moiety that facilitates an acylation reaction with the ricinoleic acid or ester or salt thereof.

15. The process of claim 14, wherein the reaction to form the intermediate takes place in a solvent.

16. The process of claim 14, wherein the $C_2$-$C_{10}$ carboxylic derivative is a carboxylic derivative having a halide, carbonate, heteroatom or imidazole leaving group.

17. The process of claim 1, wherein the intermediate is formed by reacting a $C_2$-$C_{10}$ carboxylic acid with the ricinoleic acid or ester or salt thereof.

18. The process of claim 1, wherein the intermediate is formed by reacting an ester of a $C_2$-$C_{10}$ carboxylic acid with the ricinoleic acid or ester or salt thereof.

19. The process of claim 18, wherein the reaction to form the intermediate is catalyzed by a base.

20. The process of claim 19, wherein the base catalyst is an alkali or alkaline earth alkoxide salt.

21. The process of claim 20, wherein the cation of the alkoxide salt is selected from the group consisting of sodium, potassium and calcium.

22. The process of claim 18, wherein the ester is a $C_2$-$C_{10}$ alkyl ester of a $C_2$-$C_{10}$ carboxylic acid.

* * * * *